United States Patent [19]

Roy et al.

[11] Patent Number: 4,666,833

[45] Date of Patent: May 19, 1987

[54] PROCESS FOR THE PRODUCTION OF A DIAGNOSTIC DEVICE FOR THE DETECTION OF INCREASED DEHYDROGENASE

[75] Inventors: Asok K. Roy, Berlin; Roland W. Steinbach, Cologne, both of Fed. Rep. of Germany

[73] Assignee: Medi-Pharma Vertriebsgesellschaft mbH, Fed. Rep. of Germany

[21] Appl. No.: 523,394

[22] Filed: Aug. 15, 1983

[30] Foreign Application Priority Data

Aug. 23, 1982 [DE] Fed. Rep. of Germany ....... 3231287

[51] Int. Cl.⁴ .................. C12Q 1/32; C12N 9/96; B65D 69/00; A61F 13/16
[52] U.S. Cl. .................. 435/26; 435/188; 435/805; 206/569; 206/829; 604/361; 604/362; 604/904
[58] Field of Search .............. 435/26, 805, 188; 604/361, 362, 904; 206/569, 829

[56] References Cited

U.S. PATENT DOCUMENTS

| | | | |
|---|---|---|---|
| 2,897,600 | 8/1959 | Graham et al. | 435/188 |
| 3,539,450 | 11/1970 | Deutsch | 435/188 |
| 3,867,259 | 2/1975 | Forgione | 435/26 |
| 4,056,485 | 11/1977 | Adolf et al. | 435/26 |
| 4,266,022 | 5/1981 | Lamprecht | 435/26 |
| 4,289,824 | 9/1981 | Smith | 604/904 |
| 4,361,648 | 11/1982 | Shuenn-tzong | 435/805 |

FOREIGN PATENT DOCUMENTS

| | | | |
|---|---|---|---|
| 1360969 | 7/1974 | United Kingdom | 435/188 |
| 1433415 | 4/1976 | United Kingdom | 604/361 |
| 2081586 | 2/1982 | United Kingdom | 604/904 |

OTHER PUBLICATIONS

Mahler, et al., eds., Biological Chemistry, 2nd ed. (1971), Harper & Row, Pub., p. 30.
Curtius, et al., eds., Clinical Biochemistry, vol. 1, 1978, Walter de Gruyter, Pub., p. 478.

*Primary Examiner*—Christine M. Nucker
*Assistant Examiner*—Stephen Wieder
*Attorney, Agent, or Firm*—Dressler, Goldsmith, Shore, Sutker & Milnamow, Ltd.

[57] ABSTRACT

A process for the production of a diagnostic device which is envisaged, in particular, for the detection of a pathologically increased concentration of dehydrogenases in fluids of humans, animals or plants and consists of a carrier and a substance mixture, in which, in each case with exclusion of UV radiation, the substance mixture, which has been adjusted to a pH value in the acid range, is brought into contact, in liquid form, with the carrier and the combination of carrier and substance mixture is subsequently dried and then enclosed in a packaging casing which is opaque to light of higher energy than red light. The process has the peculiarity that the dried combination of carrier and substance mixture in the packaging casing is securely sealed against entry of air and moisture. The device thus produced can be stored for a long time before use, without its ability to function being substantially changed.

12 Claims, 4 Drawing Figures

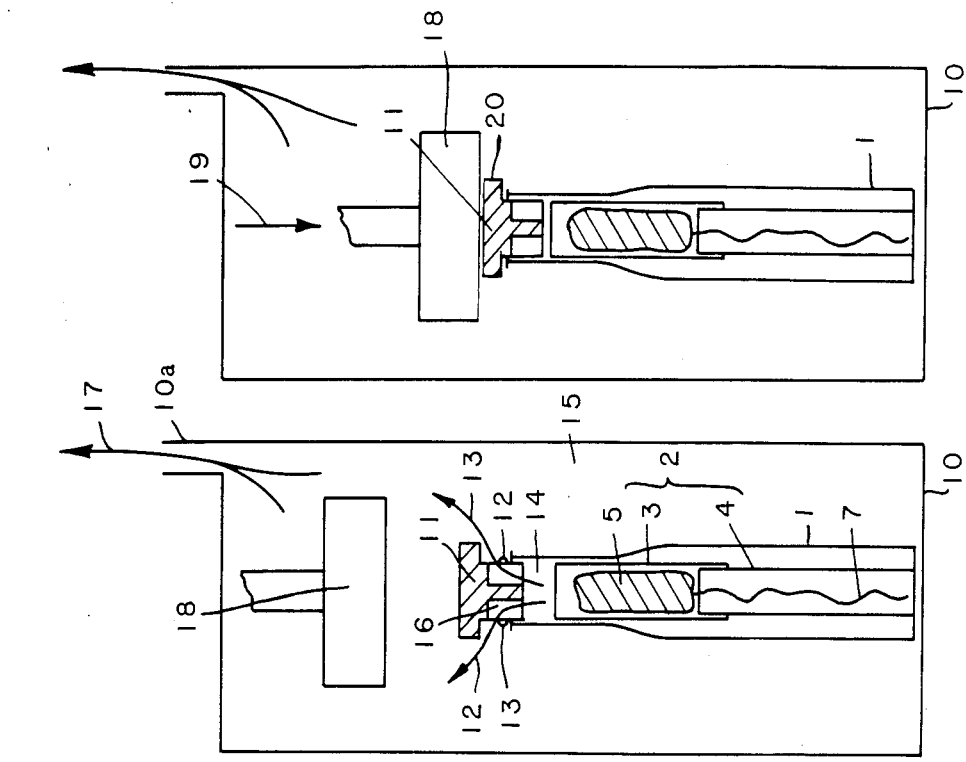
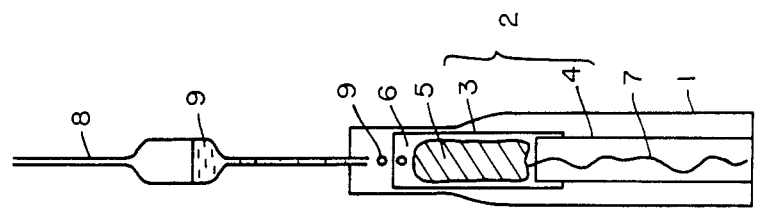
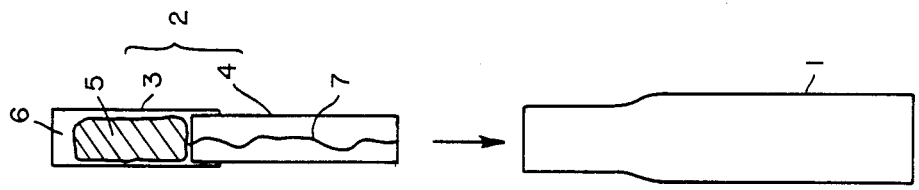

PROCESS FOR THE PRODUCTION OF A DIAGNOSTIC DEVICE FOR THE DETECTION OF INCREASED DEHYDROGENASE

The invention relates to a process for the production of a diagnostic device which is envisaged, in particular, for the detection of a pathologically increased concentration of dehydrogenases in fluids of humans, animals or plants and consists of a carrier and a substance mixture.

Medical diagnoses play a considerable role in the health service. This particularly applies to diagnoses in the context of screening tests. Diagnoses have already achieved a great practical importance here, for example for early diagnosis of malignant growths, since the prospects of therapeutic success are highest with timely diagnosis of such a disease.

Pathological changes in humans, animals or plants can influence the composition of extra-cellular fluids of these organisms. For example, when cells undergo pathological changes, as is the case in the formation of malignant growths, dehydrogenases pass into the serum and into other extra-cellular fluids. A threshold value which can be considered pathological and is diagnostically useful can be found for each dehydrogenase.

It is already possible to describe chemical diagnosing agents which have a transition point matching the pathological threshold value of a dehydrogenase. The passing of this transition point can be rendered visible, for example, by means of a redox dyestuff which is contained in the diagnostic agent and changes from colorless to colored at the pathological threshold value.

A diagnosing agent which is envisaged for the detection of a pathologically increased concentration of dehydrogenases in extra-cellular fluids contains, for example, a substance mixture, adjusted to a pH value in the acid range, of the substrate corresponding to the particular dehydrogenase, a hydrogen donor compound and at least one redox dyestuff. So that the agent is suitable for differential diagnostics, in which only pathologically increased dehydrogenase concentrations are recorded, the pH value mentioned must be fairly low, for example below 5.0.

For certain types of diagnosis, such as intracorporal examinations, it is necessary to apply the diagnostic agent to a carrier before its use. This applies to, for example, diagnoses in the case of women who are to be examined for the presence of carcinomas in the genital area. For this purpose, it is known, from German Patent Specification No. 2,443,741, to apply the diagnostic agent to a hygiene tampon and to insert it in this form into the vagina of the patient, where the agent can react with dehydrogenases contained in the vaginal secretion. If the tampon shows discoloration after its removal from the vagina, this is an indication of a pathological change in the body of the patient.

German Patent Specification No. 2,443,741 discloses, inter alia, a process for the production of a diagnostic device which consists of a tampon and a substance mixture applied thereto. The device is envisaged for joint determination of the isoenzymes 4 and 5 of lactate dehydrogenase and, finally, is intended for use for the diagnosis of pathological changes in the lower genital tract in women.

In this known production, the substance mixture, adjusted to a pH value in the acid range, is brought into contact, in liquid form, with the tampon, in each case under the exclusion of high-energy light. The combination of tampon and substance mixture is then dried and subsequently enclosed in a packaging casing opaque to high-energy light.

In this context and also in the following text, "high-energy light" means light (including UV light) which is of a higher energy than red light.

In practice, it has been found that certain properties of the diagnostic device are particularly desirable.

The invention is thus based on the object of providing a process for the production of a diagnostic device which can be stored for as long as possible before use, without its ability to function thereby substantially changing; for example, if the device contains a redox dyestuff, it should not tend to discolor prematurely during storage. Moreover, the diagnostic device should achieve a high diagnostic accuracy during as short a use time as possible (residence time) on the patient. Moreover, in cases where the diagnostic agent forms a dyestuff when used intracorporally, as firm as possible a bonding of the dyestuff to the carrier of the diagnostic device should be sought, in order to avoid transfer of this dyestuff, for example, into the vaginal skin of a woman examined. Finally, the time required for production of the diagnostic device should be shortened.

This object is achieved, according to the invention, by a process for the production of a diagnostic device comprising a carrier and a substance mixture, in which, in each case with exclusion of high-energy light, the substance mixture, which has been adjusted to a pH value in the acid range, is brought into contact, in liquid form, with the carrier and the combination of carrier and substance mixture is subsequently dried and then enclosed in a packaging casing which is opaque to high-energy light. The process is characterised in that the dried combination of carrier and substance mixture in the packaging casing is securely sealed against the entry of air and moisture.

According to a preferred embodiment of the process, a carrier, which bonds a redox dyestuff, and a substance mixture of the substrate corresponding to the particular dehydrogenase to be detected, a hydrogen donor compound, at least one redox dyestuff and, if appropriate, a buffer system are used, the process being characterised in that the carrier has polar groups and the substance mixture is adjusted to a pH value of below 5.0. A diagnostic device is thus obtained which is particularly suitable for differential diagnostics for the detection of pathologically increased dehydrogenase concentrations and, in addition to having a long storage life, has a high diagnostic accuracy for a relatively long time, for example more than two years.

In a particular development of the process, a tampon containing cellulose fibers is used as the carrier. The diagnostic device thus prepared proves particularly suitable for intracorporal examinations, such as diagnoses of carcinomas in the genital area of women. This diagnostic device can be stored for several years before use, achieves high diagnostic accuracy, inspite of a short residence time of at most 10 minutes in the patient, and guarantees firm bonding of the dyestuff which may be formed during diagnosis to the cellulose fibers of the tampon, so that transfer of the dyestuff into the vaginal mucous membrane of the patient examined is non-existent.

Tampons of cellulose fibers have proved particularly suitable for those diagnostic devices envisaged for detecting carcinomas in the female genital area. The conventional hygiene tampons can be used for this. These are preferably not wound, but have a longitudinal seam. The cellulose fiber tampons have the particular advantage that bonding to the dyestuff formed when the diagnostic device is used is particularly strong, the polar groups of the cellulose material and corresponding polar groups in the dyestuff probably undergoing firm bonding.

Experiments in which attempts have been made to dissolve the dyestuff (formazan) out of the tampon show the strength of bonding between the cellulose fibers and the dyestuff. Four different media were used as extracting agents: a. physiological saline solution, b. a solution containing human albumin and mucin for imitation of vaginal secretion (which cannot be obtained in a sufficient amount), c. a solution according to b., which additionally contained a surface-active substance, for example sodium lauryl-sulfate, and d. chloroform.

It was not possible to dissolve relatively large amounts of the dyestuff (formazan) out of the tampon with any of these media. Even when the tampon was heated in boiling chloroform for six hours, only about 7% of the dyestuff (formazan) could be extracted. Since the tampon remains in a body cavity for a maximum of only 10 minutes at about 37° C. when used in human medicine, there is evidently no danger that some of the dyestuff which may be formed is extracted by the body fluid wetting the tampon and passes into the body.

The tampon can also consist of other fibers, for example hydrophilic synthetic fibers, which can be of hollow shape in order to increase their surface area and their absorbency. Tampons of a mixture of various types of fiber, for example natural and synthetic fibers, can, of course, be used as long as the fibers are hydrophilic and have polar groups.

The diagnostic device comprising a tampon is suitable not only for intracorporal diagnosis but also for extracorporal diagnosis. In the latter case, the body fluid to be examined is brought into contact with that area of the tampon containing the substance mixture mentioned.

The combination of carrier and substance mixture is preferably already located in the packaging casing before drying. In this manner, after drying, the packaging casing needs only to be sealed. Since this sealing lasts only a short time, the danger of more moisture entering the carrier and the substance mixture and impairing the life of the diagnostic device is thus avoided.

According to a particular embodiment, the packaging casing containing the carrier and the substance mixture is sealed whilst still in the drying device. This ensures that, after sealing, the inside of the packaging casing also has the low moisture content achieved by drying.

For use of the diagnostic device in the form of a tampon, it is advantageous for the tampon to be located in an applicator. This means that the tampon can be inserted into a body cavity, for example into the vagina, without direct contact with the fingers and without the danger of infection.

Accordingly, in the production of such a diagnostic device, the tampon is introduced into the insertion cartridge of the applicator. It is preferable to locate the tampon in the applicator before application of the substance mixture, because the applicator then serves as a means of holding the tampon when the substance mixture is applied thereto.

It is advantageous for the applicator to have an insertion cartridge with an inner wall which is impermeable to liquid, and for the tampon to be arranged in the insertion cartridge such that a free space is obtained within the insertion cartridge in front of the insertion end of the tampon. This space can temporarily accommodate the substance mixture to be applied to the tampon and thus contributes to an accelerated course of the process. The inner wall, which is impermeable to liquid, of the insertion cartridge of the applicator permits rapid application of the substance mixture, in liquid form, onto the tampon without some of this liquid being absorbed by the wall of the insertion cartridge or even passing through it and thus being lost to the tampon.

In an embodiment of the process which is particularly suitable in practice, a solution of the substance mixture is injected into the free space mentioned, for example by means of a metering device. This injection can be effected very rapidly, which means that the rate of production can be increased.

A small tube which is open on one side, consists of metal of high heat conductivity and has an elastic sealing plug is preferably used as the packaging casing. Such a small tube, for example of aluminium, can in turn be easily produced and ensures permanent protection of the diagnostic device from air, moisture, light and mechanical damage, after the sealing plug, which can consist of a rubber-like material, has been placed on top.

In addition, the small tube can serve as a means of holding the diagnostic device during application of the substance mixture onto the carrier.

Finally, the high heat conductivity of the material of the small tube favours rapid transfer of heat between the individual small tubes. This is advantageous if, when each of the small tubes have been charged with a diagnostic device, they are dried with their contents, whilst in contact with one another.

In a development of this process variant, the small tube is charged with the combination of applicator and tampon, the substance mixture is then applied to the tampon and the small tube is subsequently partly sealed with the sealing plug and dried with its contents. Partial sealing of the small tube permits, on the one hand, the desired drying and, on the other hand, rapid complete sealing of the small tube after drying, which can even be effected whilst the tube is still within the drying device.

To achieve a particularly long life of the packaged diagnostic devices, the carrier and substance mixture are dried in a freeze-drying device and the packaging casing is then sealed in this device under the reduced pressure which had already been established for the drying operation in the freeze-drying device.

Freeze-drying is particularly recommended for the present process, since the material to be dried is relatively rapidly and substantially freed from the solvent for the substance mixture.

Rapid drying favours very fine distribution of the substance mixture on the carrier. This means that, after drying, the substance mixture is bonded to the carrier chiefly in amorphous form and not in the form of relatively large crystals. Bonding between the individual constituents of the substance mixture, in particular the dyestuff component, and the carrier is thereby increased.

In addition, volatile constituents, for example water, are also removed from the carrier, for example the cellulose fibers of the tampon, during freeze-drying, which means that the spatial conditions for the molecules of the dyestuff component are improved further for coming in as close as possible a contact with the molecules of the carrier. A relatively large number of covalent bonds between the dyestuff and carrier result. The danger of dyestuff molecules being dissolved out of the carrier by body fluids is thereby greatly reduced.

It has also been found that, as a result of the firm bond between the carrier and the dyestuff, the color reaction which takes place when the diagnostic device is used proceeds particularly specifically at a desirable pH value of below 5.0, and the accuracy of the diagnosis is thereby considerably increased.

The firm bond between the substance mixture and carrier achieved by freeze-drying is also the cause of the long life of diagnostic devices produced in this manner.

Optimum freeze-drying of the diagnostic device is effected if the device is dried in a first stage under a relatively slightly reduced pressure and in a second stage under a more greatly reduced pressure. This promotes removal of, for example, water molecules contained in the carrier independently of the substance mixture applied. The relatively slightly reduced pressure for predrying is of the order of about 1.33 Pa ($10^{-2}$ mm hg). In the subsequent stage of after-drying, the more greatly reduced pressure is adjusted to about 0.13 Pa ($10^{-3}$ mm hg).

The diagnostic device has a long life if it is dried down to a moisture content of less than 1% inside the packaging casing. In this case, the diagnostic device can be stored for more than $3\frac{1}{2}$ years before being used, without its ability to function being substantially impaired.

The process according to the invention and the storage life of diagnostic devices produced in this manner are illustrated by way of example in the following text.

EXAMPLE 1

The individual components of the substance mixture are weighed out, and dissolved in distilled water with exclusion of high-energy light, for example under red light. Exclusion of high-energy light is also ensured for the subsequent process stages.

The carrier for the substance mixture is a conventional hygiene tampon of cellulose fibers. It is arranged in the insertion cartridge of a tampon applicator, into which cartridge an ejection cartridge with a somewhat smaller external diameter is partly pushed telescopically. Both cartridges of the applicator are produced, for example, of wound cardboard or plastic. Such applicators are commercially available.

The ejection cartridge is prevented from unintentionally sliding out of the insertion cartridge by means of an impression in the area where the insertion cartridge and the ejection cartridge of the applicator overlap.

The tampon is pushed into the applicator via the insertion end of the insertion cartridge, such that it lies against the front end of the ejection cartridge and at the same time a free space of about 3 cm³ or with an axial length of about 3 cm is obtained within the insertion cartridge before the insertion end of the tampon. The recovery thread of the tampon extends from the back end of the tampon inside the ejection cartridge to beyond the back end of the latter.

The arrangement of applicator and tampon is introduced into a small packaging tube of aluminium such that the insertion end of the applicator and the opening of the small tube point upwards.

About 2 ml of the aqueous solution of the substance mixture prepared above are then injected into the top of the free space mentioned within the insertion cartridge and in front of the insertion end of the tampon by means of a metering device.

To increase the rate of production, this injection takes place so rapidly that, for a short time, some of the solution remains in the free space mentioned in the applicator before it is completely absorbed by the tampon. In order to prevent some of the solution penetrating into the water-soluble or water-absorbing wall of the insertion cartridge, and thus being lost to the tampon, during this time and also even after absorption onto the tampon, the inner wall of the insertion cartridge is coated with a substance which is impermeable to liquid, for example an aluminum or PVDC film.

The solution of the substance mixture causes the tampon to swell within the applicator. Since the tampon is already adjacent to the insertion end of the ejection cartridge and expansion of the tampon towards the back end of the applicator is prevented because the ejection cartridge is fixed by means of the impression mentioned, the tampon softens out in the direction of the insertion end of the applicator as its volume enlarges by absorption of liquid, and thereby substantially fills the free space mentioned in the insertion cartridge of the applicator.

A plug of an elastic material is then partly placed over the opening of the small packaging tube. The plug is thereby pushed in to the small tube up to a first projection on its circumference. With the plug in this position, a flow channel remains free between the interior of the small tube and its external environment by means of a depression in the plug.

A large number of small packaging tubes prepared in this manner are placed side-by-side in contact with one another and introduced into a freeze-drying device.

In this device, the small tubes and their contents are pre-frozen and then pre-dried in a first drying stage under a reduced pressure of about 1.33 Pa. In a second drying stage, the material to be dried is after-dried at a more greatly reduced pressure of 0.13 Pa. The total drying time is about 24 hours.

When a residual moisture of less than 1% is achieved, the small packaging tubes are sealed in the freeze-drying device under the prevailing reduced pressure. This is effected by hydraulic lowering of a sealing plate which pushes in the sealing plugs of the small packaging tubes up to a second projection on the circumference of each plug and thereby completely seals the small tubes.

The small packaging tubes can then be removed from the freeze-drying unit and exposed to ambient conditions, such as air, usual moisture and high-energy light, without the packaged diagnostic devices being impaired.

The specific embodiment of the process of this invention as described in claim 1 is illustrated in the accompanying FIGS. 1–4.

FIG. 1 shows a longitudinal cross section of a packaging tube 1 of aluminum and above a longitudinal cross section of a tampon applicator 2 consisting of an insertion cartridge 3 and an ejection cartridge 4. A tampon 5 is disposed inside the insertion cartridge 3, such that it lies against the front end of the ejection cartridge 4 and at the same time a free space 6 of about 3 cm³ is obtained within the insertion cartridge 3 before the insertion end of the tampon 5. The recovery thread 7 of the tampon 5 extends from the back end of the tampon 5 inside the ejection cartridge 4 to beyond the back end of the latter.

FIG. 2 shows the arrangement of applicator 2 and tampon 5 being introduced into the packaging tube 1.

By means of a pipet 8 there are injected about 2 ml of an aqueous solution 9 of a substance mixture into the free space 6 mentioned, within the insertion cartridge 3 and in front of the insertion end of the tampon 5.

FIG. 3 shows the arrangement of applicator 2 and tampon 5 placed within a freeze-drying device 10. Over the opening of the packaging tube 1 there is partly placed a plug 11 of an elastic material. The plug 11 is pushed into the packaging tube to a first projection 12 on its circumference. With the plug 11 in this position, a float channel, indicated by arrows 13 remains free between the interior 14 of the packaging tube 1 and its external environment 15 by means of a depression 16 in the plug 11. Within the freeze-drying device 10 there is generated a reduced pressure, air and moisture being pumped out from inside the tampon 5, the applicator 2, the packaging tube 1 and the freeze-drying device 10, through outlet 10a of the freeze-drying device 10, as indicated by arrow 17. Within the freeze-drying device 10 and spaced above the plug 11, there is provided a pressure stamp 18.

FIG. 4 shows the last process step. After the whole content of the freeze-drying device 10 has been pre-frozen and then pre-dried in a first drying stage under reduced pressure, and after-dried at a more gradely reduced pressure, the packaging tube 1 is sealed within the freeze-drying device 10 under the prevailing reduced pressure. This is effected by hydraulic lowering of said pressure stamp 18, as shown by arrow 19. The pressure stamp 18 pushes in the plug 11 of the packaging tube 1 up to a second projection 20 on the circumference of said plug 11 and thereby completely seals the packaging tube 1.

The packaging tube 1 can be then be removed from the freeze-drying device 10 and exposed to ambient conditions, such as air, usual moisture and high-energy light, without the packaged diagnostic device being impaired.

It should be noted that the preparing of the aqueous solution 9 and its injection onto the tampon 5 (see FIG. 2) as well as the drying and sealing steps (see FIGS. 3 and 4) are carried out with exclusion of UV-radiation.

Specific examples in respect of the composition of the substance mixture and the life of the diagnostic devices produced are described below.

EXAMPLE 2

Diagnostic devices are produced according to Example 1. The carrier used is a conventional hygiene tampon which consists of cellulose fibers and is not wound but comprises several cellulose fiber layers which are sewn to one another together with a recovery tape in the longitudinal direction of the tampon and have then been compressed to the final tampon shape.

The substance mixture is applied to the tampon in the form of an aqueous solution of the following composition:

| Constituent | Amount |
| --- | --- |
| Sodium DL-lactate | 57.6 mg |
| Nicotinamide adenine dinucleotide | 3.0 mg |
| 2,2'-Azino-bis[3,3'-ethyl-benzthiazolin-6,6'-sulfonic acid] (MTT) | 272.5 micro g |
| Triethanolamine | 39.8 mg |
| PMS | 10.0 micro g |
| Water, purified, to | 2.0 g |

The pH value of the solution is adjusted to 4.0 with 3N hydrochloric acid.

Diagnostic devices which are still capable of functioning after several years are obtained by the the above process.

EXAMPLE 3

Diagnostic devices are prepared according to Example 1, using an aqueous solution of the substance mixture of the following composition:

| Constituent | Amount |
| --- | --- |
| Sodium DL-lactate | 57.6 mg |
| NAD | 3.0 mg |
| NBT | 556.0 micro g |
| Diaphorase | 6.4 ie |
| Triethanolamine | 39.8 mg |
| Water, purified, to | 2.0 g |

The pH value of the solution is adjusted to 4.9.

The diagnostic devices obtained with this solution can be used and kept in the same manner as the devices produced according to Example 2.

EXAMPLE 4

Diagnostic devices are produced according to Example 1, using an aqueous solution of the substance mixture of the following composition:

| Constituent | Amount |
| --- | --- |
| Sodium DL-lactate | 57.6 mg |
| NAD | 3.0 mg |
| NBT | 50.0 micro g |
| Meldola blue | 2.5 micro g |
| Triethanolamine hydrochloride | 50.0 mg |
| Water, purified, to | 2.0 g |

The pH value of the solution is 4.0.

The diagnostic devices obtained with the solution have the same properties as the devices produced according to Examples 2 and 3.

EXAMPLE 5

Diagnostic devices are produced according to Example 1, using an aqueous solution of the substance mixture of the following composition:

| Constituent | Amount |
| --- | --- |
| Sodium DL-lactate | 37.0 mg |
| NAD | 2.0 mg |
| NBT | 490.0 micro g |
| PMS | 48.7 micro g |
| Triethanolamine HCl | 49.0 mg |
| Water, purified, to | 2.019 g |

The solution is adjusted to a pH value of 4.5 with 3N hydrochloric acid.

The properties of the resulting diagnostic devices correspond to those of the devices according to Examples 2 to 4.

EXAMPLE 6

| Constituent | Amount |
| --- | --- |
| Sodium DL-lactate | 25.6 mg |
| NAD | 1.33 mg |
| TNBT | 555.0 micro g |

-continued

| Constituent | Amount |
| --- | --- |
| PMS | 30.3 micro g |
| Triethanolamine HCl | 49.0 mg |
| Water, purified, to | 2.0 g |

The solution is adjusted to a pH value of 4.0 with 3N HCl.

EXAMPLE 7

Diagnostic devices produced according to Example 1 are stored in the packaged state for various periods of time, and their ability to function is then tested.

After the appropriate storage time, the tampons are removed from their packaging in the dark and in each case brought into contact with 2 ml of a test solution in a test-tube.

The test solution is in all cases a phosphate buffer solution with a pH value of 7.5. A first group of these 2 ml samples of test solution is used, as pure phosphate buffer solution, for determining the blank values of the tampons of varying age. In each case three International Units (IU) of lactate dehydrogenase (LDH) are additionally added to a second group of the 2 ml samples of test solution. A third group of 2 ml samples of test solution is modified with in each case 1% of albumin, 0.9% of sodium chloride and 0.1% of mucin. In addition to the albumin, the sodium chloride and the mucin in the abovementioned amounts, three IU of LDH are also added to a fourth group of the 2 ml samples of test solution.

All of the abovementioned 2 ml samples of test solution in each case represent an imitation of a body fluid in this test of the ability of the tampons to function in vitro.

All the testing is carried out at room temperature and with exclusion of high-energy light. Each sample (tampon and test solution in the test-tube) is evaluated visually in response of the intensity of a possible discoloration of the tampon 20 minutes after the tampon has been wetted with the test solution, and is also photographed so that this evaluation can later be checked.

The results are summarized in the Table which follows:

TABLE

| Tampon | | Test solution | | | |
| --- | --- | --- | --- | --- | --- |
| pH value of the substance mixture | Storage time | Only buffer (blank sample) | Buffer, LDH | Buffer, Albumin, NaCl, Mucin | Buffer, Albumin NaCl, Mucin LDH |
| 4.5 | 1 year | (−) | + | | |
| 4.5 | 1 year | (−) | + to ++ | (−) to yellow | + to ++ |
| 4.5 | 1½ years | (−) | + to ++ | (−) | + to ++ |
| 4.5 | 2 years | (−) | + | | |
| 4.5 | 2½ years | (−) | (+) to + | | |
| 4.5 | 3 years | (−) | + to ++ | | |
| 4.5 | 3½ years | (−) | + to ++ | (−) | (+) to + |

(−) = no discoloration = diagnosis negative
(+) = pink = diagnosis still negative
+ = light blue with violet tinge = diagnosis positive
++ = blue = diagnosis positive From this, it can be seen that the diagnostic device with a tampon as the carrier is still capable of functioning even after a storage time of 3½ years. This is also true independently of whether the tampon consists only of cellulose fibers or a mixture of cotton and cellulose fibers or only of cotton fibers.

The carrier used according to the invention does not absolutely have to consist of fibers. For example, it can also be composed of a foam or of a film which is wound up or shaped in another manner. It is only necessary for the carrier to be sufficiently hydrophilic, so that it can absorb the body fluid to be examined when the diagnostic device is used. It is also important that the firm bonding mentioned occurs between the carrier and the dyestuff component of the substance mixture.

According to the invention, the diagnostic device is preferably packaged in a light-tight, moisture-tight and air-tight package under greatly reduced pressure, which is advantageously effected immediately after freeze-drying whilst the package is still in the freeze-drying device. However, entry of air and moisture can also be avoided another way. For example, after drying, the packaging casing with the diagnostic device therein can be filled with dry nitrogen and sealed. It is also possible for a drying agent, for example a molecular sieve, to be arranged in the packaging casing in addition to the diagnostic device.

We claim:

1. In the process for the production of a diagnostic device for the detection of a pathologically increased concentration of dehydrogenases in fluids of humans, animals or plants and which consists of a carrier and a substance mixture wherein a substance mixture in liquid form and at an acid pH value is brought into contact with a carrier in an environment which excludes UV radiation, and the combination of carrier and substance mixture is subsequently dried and enclosed in a package casing which is opaque to light of higher energy than red light, the improvement wherein said drying is carried out to a moisture content of less than 1% and said package casing is securely sealed against entry of air and moisture.

2. Process according to claim 1, in which a carrier, which bonds a redox dyestuff, and a substance mixture of the substrate corresponding to the particular dehydrogenase, a hydrogen donor compound, at least one redox dyestuff and, if appropriate, a buffer system are used, characterised in that the carrier has polar groups and the substance mixture is adjusted to a pH value of below 5.0.

3. Process according to claim 1 or 2, characterised in the a tampon containing cellulose fibers is used as the carrier.

4. Process according to claim 1, characterised in that the combination of the carrier and the substance mixture is already located in the package casing before drying.

5. Process according to claim 4, characterised in that the packaging casing is sealed in the drying device.

6. Process according to claim 5, characterised in that the tampon is located in a tampon applicator before application of the substance mixture.

7. Process according to claim 6, characterised in that the applicator has an insertion cartridge with an inner wall which is impermeable to liquid and the tampon is arranged in the insertion cartridge such that a free space is obtained within the insertion cartridge in front of the insertion end of the tampon.

8. Process according to claim 7, characterised in that a solution of the substance mixture is injected into the free space.

9. Process according to claim 1, characterised in that a small tube which is open on one side, consists of metal of high heat conductivity and has an elastic sealing plug is used as the packaging casing.

10. Process according to claim 9, characterised in that the small tube is charged with the combination of applicator and tampon, the substance mixture is then applied to the tampon and the small tube is subsequently partly sealed with the sealing plug and dried, together with its contents.

11. Process according to claim 1 characterised in that the carrier and the substance mixture are dried in a freeze-drying device and the packaging casing is then sealed in this device under greatly reduced pressure.

12. Process according to claim 11, characterised in that drying is carried out in a first stage under a relatively slightly reduced pressure and then in a second stage under a more greatly reduced pressure.

* * * * *